United States Patent [19]

Roy

[11] 4,203,921
[45] May 20, 1980

[54] STABILIZED REAGENTS

[75] Inventor: Ram B. Roy, Spring Valley, N.Y.

[73] Assignee: Technicon Instruments Corporation, Tarrytown, N.Y.

[21] Appl. No.: 956,007

[22] Filed: Oct. 30, 1978

[51] Int. Cl.² ............................................. C07C 127/00
[52] U.S. Cl. ............................. 260/553 A; 260/340.7; 260/566 F; 260/577
[58] Field of Search ..................................... 260/553 A

[56] References Cited

U.S. PATENT DOCUMENTS

| 3,558,435 | 1/1971 | Rey et al. | 260/553 A |
| 3,646,135 | 2/1972 | Coles et al. | 260/553 A |
| 3,660,484 | 5/1972 | Martin et al. | 260/553 A X |

*Primary Examiner*—Ethel G. Love
*Attorney, Agent, or Firm*—S. P. Tedesco; R. S. Salzman

[57] ABSTRACT

A class of reagents are synthesized from an aminobenzaldehyde base compound. The reagents are stable, sensitive, and useful in quantitative and qualitative analyses for: primary aromatic and aliphatic amines, reactive compounds containing methylene and amido (e.g., urea) groups; amino acids, enzymes, and immunoreactants.

2 Claims, No Drawings

STABILIZED REAGENTS

FIELD OF INVENTION

This invention relates to reagents, and methods of synthesizing the reagents, which are useful in quantitative and qualitative analyses.

BACKGROUND OF THE INVENTION

It is known that aminobenzaldehydes such as p-dimethylaminobenzaldehyde (PDMAB) are useful in many colorimetric analyses. These analyses include tests for: urea; primary and secondary aromatic and aliphatic amines; aromatic nitro, nitroso, azo compounds, hydroxyproline, tryptophan, aminopeptidase in serum, pyruvic acid, and pyrogallol. In general, amines and their salts condense with PDMAB to yield colored Schiff bases according to the following reaction.

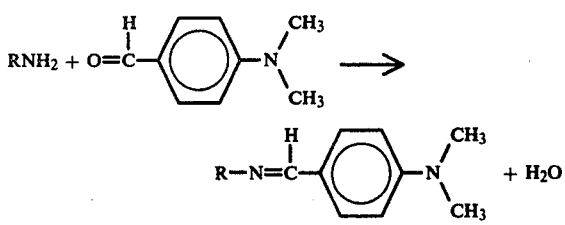

With monoanimes, the Schiff bases are yellow whereas di- and polyamines yield orange Schiff bases. The reaction product has a more intense color when the reaction takes place in a dilute acid solution, due to the protonation of the —N=CH— group.

PDMAB has also found use in fluorometric analyses; in the extraction of water insoluble alkaloids from the ergot fungus; and in the analyses of organic intermediates for the synthesis of hydrazine.

PDMAB, while extremely useful in these aforementioned tests, has one major drawback. The PDMAB reagent will readily oxidize with air contact in the dry form, and is also unstable in aqueous and acidic solutions.

Therefore, PDMAB has a short shelf life, and when acidified must be used immediately.

One aspect of this invention features a way of stabilizing aminobenzaldehydes such as PDMAB, and further teaches the synthesis of new and useful reagents derived from the stabilized aminobenzaldehyde base compound.

The invention pertains to the stabilization of an aminobenzaldehyde reagent of the general formula:

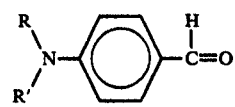

wherein R and R' are the same or different and each is selected from a group consisting of: H and a lower alkyl.

The stabilization is accomplished by reacting the above base compound with a glycerol or glycol to yield a compound of the following general formula:

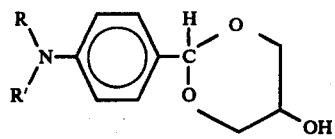

This compound may be protonated by the addition of sodium bisulfite to increase its sensitivity. The protonated compound may then be reacted with urea according to the following reaction to yield a class of complex compounds "X":

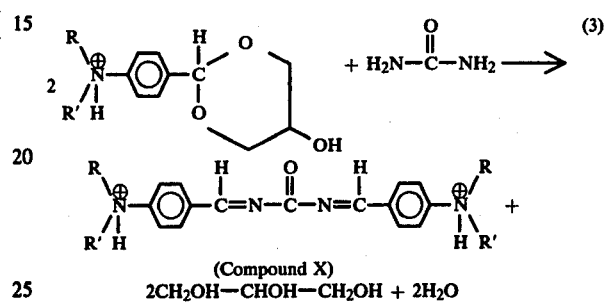

The complex compounds "X" are useful in the analysis of aromatic amines, such as aniline. The complex compounds "X" are very sensitive and are able to react with aliphatic and aromatic amines in a range of ppm/ppb.

Two commonly used reagents for amine analysis comprise fluorescamine and O-phthaldehyde. These reagents are extremely costly, and are also unstable. The compounds "X", however, are stable and are not expensive or difficult to make. According to the above teachings, its preparation can be easily achieved online in a flow system such as a colorimeter.

The complex compounds "X" contain a very reactive

group, which when reacted with aromatic compounds having an amine or methylene grouping, or with conjugated aromatic compounds with similar reactive side chains, will yield other new and useful highly conjugated complex compounds "Y", according to the following reaction:

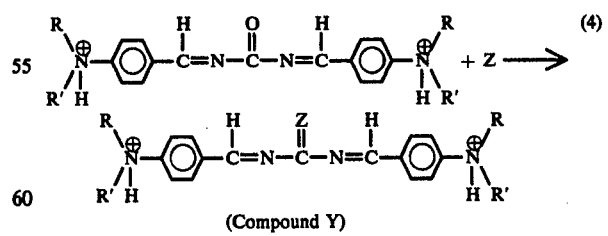

where Z is selected from aromatic and conjugated aromatic compounds, e.g., aniline, $\alpha$ and $\beta$ naphthalenamine, benzidine, carcinogenic aromatic amines containing either primary or secondary amino groups.

The highly conjugated compounds "Y" are useful as easily synthesized, low cost, fluorometric reagents. These reagents may be useful in immunoassays.

The reactant compound of Eq. 3 is also reactive with compounds containing reactive methylene groups according to the following reaction.

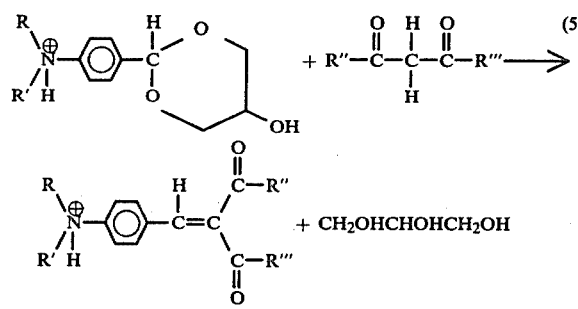

wherein R, R', R" and R"' are the same or different and each is selected from a group consisting of: H and a lower alkyl.

Specifically, the preferred base aminobenzaldhyde compound of Eq. 1, is PDMAB, i.e., R and R' are both methyl groups. This substance may be reacted with, and dissolved in glycerol or glycol by warming the mixture gently in a hot water bath at a temperature of approximately 55°–70° C. An equimolecular amount of sodium bisulfite ($NaHSO_3$) or other related compound, e.g., $KHSO_3$, $H_2SO_3$, dilute HCl, oxalic acid, etc., may then be added to protonate the nitrogen. Gentle heating may be required to dissolve the sodium bisulfite.

The resulting stabilized reagent has a syrupy appearance. It may be stored in a brown bottle at room temperature, or it may be refrigerated. It is not affected by light, and is stable for more than a year.

Having described the invention, what is desired to be protected by Letters Patent is presented by the following appended claims.

What is claimed is:

1. A protonated reagent of the general formula:

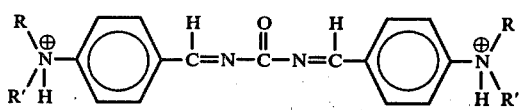

where R and R' are the same or different and each selected from a group consisting of: H and a lower alkyl.

2. The protonated reagent of claim 1, wherein R and R' are methyl groupings.

* * * * *